(12) United States Patent
Cummings et al.

(10) Patent No.: US 11,040,001 B1
(45) Date of Patent: Jun. 22, 2021

(54) COMPOSITIONS AND METHODS FOR WHITENING TEETH

(71) Applicant: JK Innovations LLC, Waltham, MA (US)

(72) Inventors: Jeffrey S Cummings, Waltham, MA (US); Karl Ginter, Beltsville, MD (US)

(73) Assignee: JK Innovations LLC, Waltham, MA (US)

( * ) Notice: Subject to any disclaimer, the term of this patent is extended or adjusted under 35 U.S.C. 154(b) by 216 days.

(21) Appl. No.: 16/129,007

(22) Filed: Sep. 12, 2018

Related U.S. Application Data

(60) Provisional application No. 62/557,459, filed on Sep. 12, 2017.

(51) Int. Cl.

| | | |
|---|---|---|
| *A61K 8/81* | (2006.01) |
| *A61K 8/42* | (2006.01) |
| *A61K 8/92* | (2006.01) |
| *A61K 8/55* | (2006.01) |
| *A61Q 11/00* | (2006.01) |
| *A61K 8/19* | (2006.01) |

(52) U.S. Cl.
CPC ............. *A61K 8/8152* (2013.01); *A61K 8/19* (2013.01); *A61K 8/42* (2013.01); *A61K 8/55* (2013.01); *A61K 8/92* (2013.01); *A61Q 11/00* (2013.01); *A61K 2800/87* (2013.01); *A61K 2800/92* (2013.01)

(58) Field of Classification Search
CPC .......... A61C 19/06; A61K 33/16; A61K 8/33; A61K 8/21
USPC .................................. 424/606, 673, 675, 676
See application file for complete search history.

(56) References Cited

U.S. PATENT DOCUMENTS

| | | | |
|---|---|---|---|
| 6,517,350 B2 | 2/2003 | Diasti et al. | |
| 6,777,459 B2* | 8/2004 | Al-Akhdar | ............... C08F 2/48 522/107 |
| 2009/0142282 A1* | 6/2009 | Kendall | ................. A61Q 11/00 424/52 |
| 2014/0248222 A1* | 9/2014 | Huo | ...................... A61K 6/0017 424/52 |
| 2015/0111172 A1* | 4/2015 | Jung | .................. A61C 13/0003 433/172 |
| 2016/0022548 A1* | 1/2016 | Allred | ...................... A61K 8/24 433/217.1 |
| 2016/0296427 A1* | 10/2016 | Young | ...................... A61K 8/31 |

* cited by examiner

*Primary Examiner* — Walter E Webb
(74) *Attorney, Agent, or Firm* — Nixon & Vanderhye PC

(57) ABSTRACT

Disclosed herein is a dental tray compound composition demonstrating an in situ formed dental tray with integrated fluoride release and whitening agents. The in situ dental tray forming compound described herein comprises at least one rosin or resin, a solvent, an optional fluoridating agent, a whitening agent, an optional re-mineralizing agent, an optional flavor additive, and optionally a sweetener. Some embodiments further include an anti-cavity agent, and more particularly a silver-based anti-cavity agent.

30 Claims, No Drawings

COMPOSITIONS AND METHODS FOR WHITENING TEETH

CROSS-REFERENCE TO RELATED PATENT APPLICATION

The present patent application claims priority to provisional U.S. Patent Application Ser. No. 62/557,459, filed 12 Sep. 2017, the entire disclosure of which is incorporated herein by reference in its entirety and for all purposes.

NOTICE OF COPYRIGHT

Portions of this patent application include materials that are subject to copyright protection. The copyright owner has no objection to the facsimile reproduction by anyone of the patent document itself, or of the patent application, as it appears in the files of the United States Patent and Trademark Office, but otherwise reserves all copyright rights whatsoever in such included copyrighted materials.

BACKGROUND OF THE INVENTION

1. Field of the Invention

The present invention provides compositions for treating teeth, and methods for applying such treatments to teeth, especially whitening and fluoridation agents. The present invention has applications in the field of dentistry and oral pharmaceuticals.

2. The Related Art

Dental health and hygiene are vital to physical well-being. Unlike the skin, the teeth are exposed to the hostile environment of the mouth, including bacteria and various chemicals, that degrade and discolor the enable of the teeth leading to dental caries, with their attendant physiological effects on the body, and disfigurement, without any significant protective systems. The results can lead to expensive, painful, and lengthy dental restoration (both physical and cosmetic).

Delivering therapeutic and prophylactic agents to the teeth effectively is not a simple task. Treatments typically require exposing tooth surfaces to compositions including a vehicle and a therapeutic agent, in which the vehicle adheres, or sticks, to the tooth surface to enable the migration of the therapeutic agent into the tooth surface. Such treatments however, take from four to six hours, during which time the patient must remain relatively immobile. Worse, the agents often include harsh chemicals such as hydrogen peroxide ($H_2O_2$)—which comprises as much as 30% of some commercial products—that irritate the gums and teeth, or require harsh light exposure to activate key ingredients, that leave patients in pain for hours.

Currently, the most effective treatments are performed in the dentist's office using a varnish composition that is painted on the tooth surface. In general, the prior art teaches that the varnish must be "soft" enough to enable easy removal from the tooth surface. Varnish formations that are "hard" are considered to have too great a risk of permanently adhering to the tooth surface.

A typical example of a varnish is described in U.S. Pat. No. 9,078,840 to Huo and Simonton, dental varnishes known in the art are generally, and typically, comprised of natural gum rosin, sodium fluoride, and various solvents, flavor additives, sweeteners, and pigments. Such dental varnishes are normally applied by a brush onto a tooth surface to prevent tooth decay by fluoride release from the composition into the adjacent tooth enamel. One of the issues with well-known dental varnishes is that the fluoride release tends to be slow, often taking more than four hours to achieve satisfactory results. This slow fluoride release results from gum rosins being used as carriers and adhesive agents: the gum rosins used in known dental varnishes are hydrophobic and therefore do not dissolve in saliva. Therefore, it generally requires at least four hours of treatment time to be able to release enough fluoride ion to be effective. Another issue of traditional varnishes that most dental varnishes are yellow and color the teeth during treatment, and patients generally prefer not to draw attention to their teeth while they are undergoing treatment.

The '840 patent further describes improved dental varnishes comprising a rosin, a resin, a fluoridating agent, a solvent, an optional re-mineralizing agent, an optional flavor additive, an optional sweetener, and optionally an oxide. These varnishes allegedly demonstrate improved fluoride release and improved transmittance of light.

However, prior art varnish compounds do not harden completely when applied to the teeth, remaining "sticky." The sticky sensation is a source of patient discomfort. The lack of hardening also supports the elution of the fluoride release as the varnish is slowly dissolved by saliva in the mouth.

Pre-made dental trays have been used to apply whitening compounds to teeth. They are created by a dentist prior to use by making a mold of the patient's teeth, and are typically used by the patient in conjunction with a liquid whitening compound. Whitening compounds are typically glycerine and hydrogen peroxide-based compounds. These compounds are held in close proximity to the teeth and whiten the teeth as the liquid compound interacts with the teeth and the bleaching agent breaks down. Dental trays require custom molding and fitting, and typically leak the peroxide-based bleaching compound onto the gums, which are in turn irritated by the bleaching compound. These whitening compounds also cause tooth sensitivity. This requires significant effort on the part of the dental professional to create the trays, protect the oral tissues, and in mitigating the suffering and pain of the user. Furthermore, these types of whitening compounds typically hydrophilic and act as drying agents which draw moisture from the teeth, which is believed to disrupt the hydrostatic equilibrium of the teeth. This hydrostatic disruption is communicated to the tooth nerve, where it is recognized as tooth pain by the user. Many attempts have been made to find a solution to this pain, including adding compounds to the whitening mixture for their analgesic and/or anesthetic properties.

In addition, traditional whitening compounds used with trays require that the trays be worn by the patient for several hours or overnight. Higher strength hydrogen peroxide compounds are also applied in the dentist office, where they take up to an hour per treatment.

What is needed is a compound and application technique that creates an in-situ hardened structure that may apply one or more orally effective compounds (the active ingredients) such as a therapeutic (e.g. fluoride, an analgesic) and/or bleaching agents directly to a treated oral surface without leakage or elution of the active compounds into the rest of the mouth and which does not cause pain to the user, either by gum irritation or by causing tooth pain. The present invention meets these and other needs.

SUMMARY OF EMBODIMENTS OF THE INVENTION

Disclosed herein is an in situ formed dental tray compound composition demonstrating an in situ formed dental tray with integrated therapeutic and/or whitening agents release. The in situ dental tray-forming compound described herein comprises at least one rosin or resin, a solvent, an optional flavoring additive, an optional sweetener, and one or more orally effective compounds selected from the set of a fluoridating agent, a whitening agent, a re-mineralizing agent, an analgesic, an anesthetic, an anti-cavity agent, more particularly, a silver-based anti-cavity agent.

In a first aspect, the present invention provides novel dental varnish compositions for application to the surface of a subject's tooth. In more specific embodiments, the compositions of the invention are used to provide in situ formed dental trays, and still more specifically dental trays to whiten teeth or provide fluoride to teeth (or both). In some embodiments, the compositions include anti-cavity agents. In yet more specific embodiments, the dental varnish compositions of the invention disintegrate within about one hour of application. In more specific embodiments, the compositions of the invention comprise at least one rosin or resin, a solvent, an optional flavoring additive, an optional sweetener, and one or more orally effective compounds selected from the set of a fluoridating agent, a whitening agent, an re-mineralizing agent, an analgesic, an anesthetic, an anti-cavity agent, more particularly a silver-based anti-cavity agent as described above and herein below.

In a second aspect, the present invention provides a method of treating a tooth surface. According to certain embodiments of the invention, a dental varnish composition of the invention is applied to the surface of a tooth for a time sufficient to provide a desired effect to the tooth. In more specific embodiments, the application time is about one hour. In still more specific embodiments, the desired effect is the whitening of the tooth surface.

In a third aspect, the compositions of the present invention are used to provide an in situ dental tray for application to one or more teeth of a patient and its subsequent release and removal from the mouth. In some embodiments, the in situ dental tray provides the benefits described herein. In other embodiments, the tray is removed by disintegration. In more specific embodiments, the disintegration of the in situ dental tray disintegrates in about one hour.

These and still more aspects and advantages of the invention will be apparent when those of skill in the art read the description and claims herein.

DETAILED DESCRIPTION OF SOME EMBODIMENTS OF THE INVENTION

| Terms and abbreviations | |
|---|---|
| Abbreviation/term | Definition |
| UC | Urea-carbamide or carbamide peroxide |
| TEGDMA | Triethylene glycol dimethacrylate |
| DUDMA | diurethane dimethacrylate |
| MPF | Sodium monosodium fluorophosphate |
| BISDMA | Bisphenol A glycidyl methacrylate |
| $H_2O_2$ | Hydrogen peroxide (in water) |
| MOIL | Mineral Oil (USP) |
| Oral surface | A surface in the mouth, e.g. a tooth, gum tissue, tooth socket, mucosa |
| Activated | The chemical process where an active ingredient in the compound undergoes a change from the form in the compound to a form that provides an effect in the oral cavity. For example, the decomposition of carbamide peroxide to urea and hydrogen peroxide. |
| Release | When the dental tray no longer adheres to the oral surface. |

The invention provides a therapeutic device-forming dental tray compound and methods for use for the delivery of cosmetic and active ingredients to the oral cavity. The delivery of these compounds to the oral cavity is faster than current techniques and also is pain-free.

The compositions of the invention comprise at least one rosin or resin, a solvent, one or more optional whitening agents, one or more optional therapeutic agents (e.g. a fluoridating agent, a re-mineralizing agent, an anti-cavity agent), an optional flavor additive, and optionally a sweetener. The components just described can be compounded and used to beneficial effect by those having ordinary skill in the art using the descriptions and instructions provided herein.

The combination of rosin and resin permits the in situ dental tray to removably form on an oral surface, and as the whitening compound is activated and/or therapeutic compound are delivered to the oral cavity, the in situ dental tray becomes permeable, and then increasing fragile as it loses structural strength, until the in situ formed dental tray detaches from the oral surface and breaks apart. Dampness of the teeth or oral cavity, rinsing with an water, or an aqueous or ethanol based solution, or by using the water produced by the activation of one or more of the included compounds is sufficient to cause the structural degradation of the in situ formed dental tray. The structural breakdown occurs over a period of 5 minutes to 4 hours. In more specific embodiments, this structural breakdown occurs in less than 1 hour, and in still more specific embodiments, the structural breakdown occurs in less than 10 minutes.

5.2 Rosin

The rosin suitable for use herein is at least a partially hydrogenated rosin, and preferably a fully hydrogenated rosin. The more hydrogenated a rosin, the more colorless it will appear to the human eye. The rosin provides the adhesion of the in situ-formed dental tray to the oral surface of a patient and is believed to facilitate its subsequent automatic release after the active ingredients are fully activated. Without the rosin, an in situ-formed dental tray may not removably adhere to the oral surface and automatically release upon completion of treatment (e.g. the elution of the active ingredients), but will adhere until manually removed. The adherence persistence of the resulting in-situ formed dental tray is proportional to the amount of rosin present in the initial formulation; changing the amount of rosin present in the mixture will change the adherence time of the in situ formed dental tray. In some embodiments, rosins suitable for use herein include those sold under the trade name FORAL AX-E® (hydrogenated gum rosin; acid number (AN) 165, available commercially from Eastman).

The rosin may be present in the in situ formed dental tray compound in amounts of about 10% to about 44% by weight. In more specific embodiments, the rosin is present in amounts from about 10% to about 33% by weight, and still more specifically from about 10% to about 18% by weight.

5.3 Solvent

Solvents suitable for use in the in situ formed dental tray forming compound described herein include one or more alcohols, one or more hydrocarbons, or combinations therein. In some embodiments, the solvent comprises a mixture of alcohol and hydrocarbons at azeotropic or near azeotropic proportions. The relative weights given above relate only to azeotropic mixtures, and are not intended to restrict the absolute or relative amounts of alcohol and/or hydrocarbon in the in situ formed dental tray compound formulations. These formulations may include individual solvents (e.g., ethyl alcohol only), or mixtures of alcohols, individual hydrocarbons or their mixtures, or mixtures of alcohols with hydrocarbons.

Alcohols suitable for use in the in situ formed dental tray compound formulations described herein include C2-C4 alcohols which can be linear, branched, or cyclic, include one or more degrees of unsaturation, and on which the hydroxyl moiety can be at any position on the carbon skeleton. Examples of suitable alcohols include, but are not limited to: ethyl alcohol, propyl alcohol (including its isomers n-propyl alcohol and iso-propyl alcohol), butyl alcohol (including its isomers, namely n-butyl alcohol, sec-butyl alcohol, iso-butyl alcohol, and t-butyl alcohol), and blends thereof. Use of alcohols outside the C2-C4 range is also contemplated, including alcohols having C5-C7 hydrocarbon skeletons, which may be linear, branched, or cyclic, and have one or more degrees of unsaturation, such as, but not limited to: C6-hydrocarbon skeletons (e.g., n-hexane, iso-hexanes, cyclohexene, and cyclohexane, 2,5-dimethylhexane, cyclohexene, and methyl cyclohexene); C5 alcohols having aliphatic skeletons including, but not limited to: iso-pentane, n-pentane, methylcyclopentane, n-heptane, methyl-1-heptene, and mixtures thereof. The foregoing also includes polyols.

The solvent may be present in the in situ formed dental tray compound in amounts of about 2% to about 20% by weight. In more specific embodiments, the solvent is present in amounts from about 2.5% to about 17.5% by weight, and still more specifically from about 2.5% to about 7% by weight.

5.4 Resin

The resin suitable for use in the in situ formed dental tray compound described herein includes a mixture of one or more acrylic type resins, including 2-Hydroxyethyl methacrylate (HEMA), 2-(Dimethylamino) ethyl methacrylate, Isobornyl methacrylate, Methyl methacrylate, 3-(Trimethoxysilyl) propyl methacrylate, (Trimethylsilyl) methacrylate, 3-(Tris (trimethylsiloxy) silyl) propylmethacrylate, 2-(Trimethylsilyloxy) ethyl methacrylate, diurethane dimethacrylate (DUDMA), triethylene glycol dimethacrylate (TEGDMA), and crosslinkers such as bisphenol A glycerolate dimethacrylate (BISDMA), Ethylene glycol dimethacrylate (EGDM), Biphenyl dimethacrylate (BPDM), 1, 6-Hexanediol dimethacrylate (HDMA), Tetraethylene glycol dimethacrylate, Bisphenol A glycerolate dimethacrylate, 9 Bisphenol A glycerolate diacrylate, Glycerol 1, 3-dimethacrylate (GDMA), 9 Polyethylene glycol diacrylates, Dipentaerythritol penta-hexa-acrylate, Ethoxylated bisphenol methacrylate (EBPADMA), Bisphenol A ethoxylate diacrylate, and Trimethylolpropane trimethacrylate (TMPTMA) (all obtainable from Sigma Aldrich). These compounds comprise the monomer and cross-linker components of the resin.

The resin mixture may be present in the in situ formed dental tray compound in amounts of about 6% to about 50% by weight. In more specific embodiments, the resin mixture is present in amounts from about 27% to about 50% by weight, and still more specifically from about 40% to about 50% by weight.

This synthesized resin in combination with a hydrogenated rosin provides the backbone for a colorless in situ dental tray forming compound as both the resin and the rosin are substantially colorless. As one of ordinary skill in the art will understand, any resin that is substantially colorless is suitable for use in the dental tray described herein.

5.5 Initiators

The resins described above may be mixed with an initiator to determine when polymerization occurs. The initiators are a class of compounds which accelerate the polymerization of the resins of the in situ formed dental tray into a hard, transparent structure when the polymerization conditions are met.

An initiator may activate when heated, exposed to oxygen, exposed to specific wavelengths of light, specific chemicals, etc. A single initiator, or a mixture of initiators may be used in the in situ formed dental tray compound. Those skilled in the art may select the initiator(s) desired for specific applications.

One class of photo-initiators causes polymerization when it is exposed to specific wavelengths of light, such as the UV light found in dental offices that is used to cure dental composites. In an embodiment, the resin is mixed with a photo-initiator selected from one or more of Diphenyliodonium Hexafluorophosphate, Diphenyliodonium chloride, diphenyl(2,4,6-trimethylbenzoyl) phosphine oxide (UV) and di-campherquinone (UV or visible light) (all available from Sigma-Aldrich).

In an alternative embodiment, the resin is mixed with a thermal initiator such as 1 phenyl-1,2 propanedione (acetyl benzoyl) or benzoyl peroxide, which are part of the class of benzoyl, organic peroxides, and azo compounds that are well known as thermal initiators. Other thermal initiators that may be used in the in situ formed dental tray include 2,2'-Azobis[2-(2-imidazolin-2-yl)-propane] Dihydrochloride and Cumene Hydroperoxide, Thermal initiators may be used for versions of the compound that initiate polymerization based upon the patient's body heat.

Some chemists use peroxide-based oxidizers as initiators. Aqueous hydrogen peroxide surprisingly inhibits the polymerization (setting) of the in situ formed dental tray compounds described herein.

The initiator may be present in the in situ formed dental tray compound in amounts of about 1% to about 10% by weight. In more specific embodiments, the initiator is present in amounts from about 1% to about 5% by weight, and still more specifically from about 1.5% to about 3% by weight.

5.6 Optional Agents

Other active ingredients may be added to the in situ dental tray forming compound to provide additional therapeutic activity when the in situ dental tray is formed on a patient's teeth. Some of these active ingredients may include:

5.6.1 Fluoridating Agent

In embodiments, fluoridating agents suitable for use in the dental tray described herein include sodium fluoride (NaF), stannous fluoride (SnF), sodium monofluorophosphate (MPF), zinc hexafluorosilicate, and sodium hexafluorosilicate. The fluoridating agent may be optionally present in the in situ dental tray forming compound in amounts (by weight percentage) of from about 0.1% to about 8%, such as from about 1% to about 7.5% or from about 2% to about 7%. One exemplary embodiment includes about 2.5% fluoridating agent by weight.

5.6.2 Bleaching Agent

In some embodiments, bleaching agents preferable for use in the dental tray include an anhydrous bleaching agent, such as carbamide peroxide, a solid (crystal) comprising parts of hydrogen peroxide and urea. Carbamide peroxide is weakly bonded, and "activates" in the presence of water to yield urea and hydrogen peroxide. The hydrogen peroxide further decomposes to water and free oxygen radicals, which provide the bleaching. Carbamide peroxide may be present in the in situ dental tray forming compound from about 18% to about 40% by weight.

Other bleaching agents may be used in place of carbamide peroxide, depending upon the intended use of the in situ formed dental tray. These bleaching agents may include sodium carbonate, sodium citrate, potassium persulfate, and calcium peroxide. Experiments show that the alternative bleaching agents may be used the same weights and ratios as carbamide peroxide.

Note that aqueous $H_2O_2$ prevents the formation of the in situ formed dental tray (demonstrated compounds N-R in formulation Table 4). Aqueous $H_2O_2$ and other liquid peroxides thus may not be used in an in situ dental tray forming compound.

In some preparations, the bleaching agent is prepared by grinding to reduce the particle size, and may be mixed with, or preferably, ground with an oil (less than about 20%) in order to prevent the bleaching agent particles from clumping or aggregating in the final mixture. In some specific preparations, the ratio of bleaching agent to oil is 2:1. Many of the synthetic and natural oils may be used; testing found that the oils work more or less interchangeably with only minor effects on the composition setting. In some embodiments, the oil used is mineral oil.

It should be noted that the oils may also be used to suspend and deliver some of the therapeutic compounds, as shown in the formulation tables.

5.6.3 Flavor Additive and Sweetener

The dental tray forming compound disclosed herein may further optionally comprise one or more sweeteners, including, but not limited to: xylitol, sorbitol, sucralose, aspartame, sodium saccharin, and mixtures thereof. Such sweeteners may be in the dental tray compound in amounts of from about 0.01% to about 2%, such as from about 0.05% to about 1.5% or from about 0.08% to about 1% by weight.

The dental tray forming compound disclosed herein may further optional comprise one or more anhydrous flavorings, such a mint or flavor ester. If included, such flavoring additives may be in the dental tray forming compound in amounts of from about 0.01% to about 5%, such as from about 0.1% to about 4%, or from about 0.7% to about 3% by weight. It should be noted that these flavorings generally comprise a substantial amount of solvents (see above) and are counted as a solvent in the formulation tables below.

5.6.4 Re-Mineralizing Agent

In some embodiments, the in situ dental tray forming compound may comprise a therapeutic compound that helps remineralize oral cavity structures or recreate dental enamel. Examples of these compounds include amorphous calcium phosphate and similar compounds. If present in an embodiment, these compounds may be present in the range of 0.1% to 4% by weight.

5.6.5 Analgesic

In some embodiments, the in situ dental tray forming compound may comprise a therapeutic compound that functions as an analgesic. Examples of these compounds include ibuprofen, diclofenac sodium, and similar compounds. If present in an embodiment, these compounds may be present in the range of 0.1% to 40% by weight.

5.6.6 Anti-Cavity Agent

In some embodiments, the invention includes a silver-based antibiotic or anti-cavity agent, such as silver diamine fluoride. In a particular embodiment, the silver-based compound is silver diamine fluoride, which also acts as a fluoridation compound.

5.6.7 Coloring Agent

In some embodiments, the in situ dental tray forming compound may comprise a compound that functions as a colorant. Examples of these compounds include titanium dioxide and similar compounds. If present in an embodiment, these compounds may be present in the range of 0.1% to 4% by weight.

The resulting in situ dental tray forming compound (when used with TiO2) may have a transparent or white color, or a substantially transparent color having a white or off-white tint. The coloring of the in situ formed dental tray may be advantageous in some uses.

5.7 Formulation

An exemplary formulation for the creation of an in situ dental tray forming follows using the recipe for compound 1 from Table 1. Other formulations as described in the formulation tables may be made by one skilled in the art by following these general instructions and adapting as necessary for the compounds being used.

5.7.1 Step 1: Create Rosin Base

Mix 68 g Foral AX-E fully hydrogenated rosin (Eastman) with 2 g of 100% peppermint oil (flavoring) and 30 g of 100% ethanol. Mix with low heat until fully dissolved. This creates a 68% rosin base with ~32% ethanol. Note that the 100% peppermint oil is nearly all ethanol as a carrier for the peppermint flavoring compounds, yielding a rosin/solvent mixture that is 70% rosin.

5.7.2 Step 1.5: Prepare the Whitening Agent

Finely grind 24 g of whitening compound (carbamide peroxide) solid to reduce its particle size. If an oil is going to be used in alternative formulations, grind the whitening compound with an oil such mineral oil (or other oil, as determined by recipe).

Step 2: Add the Optional Whitening, Colorization, Therapeutic, and Fluoridating Agents.

Combine 18 g of the whitening agent compound prepared in step 1.5 with the initiator and fluoridation compound. For compound 1, this means adding 5 g of the fluoridation compound solid (e.g. sodium fluoride (NaF)), and 2 g of diphenyl(2,4,6-trimethylbenzoyl) phosphine oxide (initiator) to the whitening agent (mixture). Add the result to 24 g of the above-described rosin base and mix.

5.7.3 Step 3: Add Resin and Cross-Linker

Separately combine 40 g DUMDA with 5 g of BISDMA and mix.

5.7.4 Step 4: Make Final Composition

Combine the results of Steps 2 and 3 and mix, producing the in situ dental tray forming compound (in liquid form). The resulting in situ dental tray forming compound may be used immediately or may be packaged and stored for later use.

In some embodiments, this step may be deferred until use to prevent premature polymerization or disadvantageous interactions between constituent components.

This results in 100 g of in situ dental tray forming compound in liquid form with the following composition by weight:

24 g (24%) by weight bleaching agent (carbamide peroxide)
5 g (5%) by weight fluoridation compound (NaF)
2 g (2%) by weight diphenyl(2,4,6-trimethylbenzoyl) phosphine oxide (photo-initiator)
16.32 g (16.32%) by weight rosin
0.48 g (0.48%) by weight flavoring
7.2 g (7.2%) by weight solvent (ethanol)
45 g (45%) resin mixture (40 g of DUDMA with 5 g of BISDMA)

5.8 Compositions

Example compositions are described in tables below. These compositions may be used in conjunction with the above formulation description to produce many variants of the in situ dental tray forming compound optimized for different uses. The attributes of the compounds are discussed pre- and post-setting.

Compositions are assessed for suitability based upon several attributes: Workability, paintability, adherence, shine, smoothness, setting, and releasability.

Workability is the ability of the compound to be mixed and whether can be applied using a brush or a sponge. Not workable means that a compound can not be fully mixed using normal compounding techniques, and effectively means that the particular compound is not suitable for an in situ dental tray forming compound. Clumpy compounds may be considered non-workable or poorly workable.

Paintability extends the workability of whether the compound can be applied using a brush or a sponge. Not paintable, very poor, and poor paintability means that a compound can not be applied to an oral structure (e.g. a tooth, a dry socket) using standard dental brushes and sponges, and effectively means that the particular compound is not suitable for an in situ dental tray forming compound. Clumpy compounds are considered to have poor paintability.

Adherence is the ability of the in situ formed dental tray to stick to the oral surface until the an effective amount of the active ingredients contained within it are dispensed into the oral cavity. Non-adherence means that the compound does not adhere to oral structures and means that the particular compound is not suitable for an in situ dental tray forming compound. A test for adherence is that the in situ formed dental tray does not dislodge from the oral surface without physical force being applied to it. Other values range from very poor to very good adherence. Very poor and poor adherence suggests that the active ingredients are not sufficiently dispensed into the oral cavity at the time the in situ formed dental tray detaches from the oral surface.

Shine is the appearance of the in situ formed dental tray. Low shine is generally not disqualifying for a compound, but higher shine scoring means the compound is more attractive to the end user.

Smoothness is a subjective surface roughness attribute of the in situ formed dental tray (e.g. after it is set). Smoothness is associated with patient comfort and the feel of the set compound. Higher smoothness scores considered better. A rough or bumpy surface translates into a poor smoothness score. Very poor and poor smoothness scores effectively means that the particular compound is not suitable for an in situ dental tray forming compound.

Setting is the attribute of the in situ dental tray forming compound to form a hard, eluting structure in the oral cavity. Setting is a function of the polymerization of the compound mixture when exposed to polymerization conditions. Setting is measured from very poor to very good, with very poor being a compound that sets irregularly or incompletely to very good being a compound that sets in a few seconds after exposure to the polymerization condition. Very poor, poor, and not setting scores effectively means that the particular compound is not suitable for an in situ dental tray forming compound.

Releasability is the attribute that describes how well a previously set dental tray releases from the oral tissue to which it is applied. Not releasing, very poor, and poor releasability scores effectively means that the particular compound is not suitable for an in situ dental tray forming compound.

Compounds which are not scored on a specific attribute have a neutral score.

These additional example compositions and their mechanical attributes are detailed below in Tables 1-10.

Table 1 details various sets of formulation ranges that range acceptable compound formulations for an in situ dental tray forming compound.

TABLE 1

Exemplary Compositions

| # | Rosin (note 0) | Whitener | Initiator (note 1) | Crosslinker | Resin | Other | Comments |
|---|---|---|---|---|---|---|---|
| 1 | 24 (70%) 16.32/ 7.2 g | 18% UC 18 g | 2% 2 g | 5% BISDMA 5 g | 45% DUDMA 45 g | .48 sweeter/ flavoring .48 g 5% NaF 5 g | good paintability, good adherence, shines |
| 2 | 30 (40%) 12 g/ 17.4 g | 18% UC 18 g | 2% 2 g | 5% BISDMA 5 g | 45% DUDMA 45 g | .6 sweeter/ flavoring .6 g | Very good paintabilily, good adherence, good shine, poor smoothness (rough) |
| 3 | 30 (40%) 12 g/ 17.4 g | 27% UC 27 g | 2% 2 g | 5% BISDMA 5 g | 36% DUDMA 36 g | .6 sweeter/ flavoring .6 g | Very good paintabilily, good adherence, good shine, poor smoothness (rough) |

TABLE 1-continued

Exemplary Compositions

| # | Rosin (note 0) | Whitener | Initiator (note 1) | Crosslinker | Resin | Other | Comments |
|---|---|---|---|---|---|---|---|
| 4 | 30 (40%) 12 g/ 17.4 g | 36% UC 36 g | 2% 2 g | 5% BISDMA 5 g | 27% DUDMA 27 g | .6 sweeter/ flavoring .6 g | Paintable, good adherence, poor shine, poor smoothness (rough) |
| 5 | 30 (60%) 18 g/ 11.4 g | 18% UC 18 g | 2% 2 g | 5% BISDMA 5 g | 45% DUDMA 45 g | .6 sweeter/ flavoring .6 g | Very good paintability, very good adherence, good shine, good smoothness |
| 6 | 30 (60%) 18 g/ 11.4 g | 27% UC 27 g | 2% 2 g | 5% BISDMA 5 g | 36% DUDMA 36 g | .6 sweeter/ flavoring .6 g | Good paintability, very good adherence, good shine, good smoothness |
| 7 | 30 (60%) 18 g/ 11.4 g | 36% UC 36 g | 2% 2 g | 5% BISDMA 5 g | 27% DUDMA 27 g | .6 sweeter/ flavoring .6 g | Paintable, good adherence, good shine, good smoothness |
| 8 | 24 (70%) 16.32/ 7.2 g | 24% UC 24 g | 2% 2 g | — | 45% DUDMA 45 g | .48% sweeter/ flavoring .48 g 5% NaF 5 g | Very good paintability, very good adherence, very good shine, very good smoothness |
| 9 | 30 (80%) 24 g/5.4 g | 18% UC 18 g | 2% 2 g | 5% BISDMA 5 g | 45% DUDMA 45 g | .6 sweeter/ flavoring .6 g | Poor paintability, good adherence, good shine, good smoothness |
| 10 | 30 (80%) 24 g/5.4 g | 27% UC 27 g | 2% 2 g | 5% BISDMA 5 g | 36% DUDMA. 36 g | .6 sweeter/ flavoring .6 g | Not paintable, good adherence, good shine, good smoothness. |
| 11 | 30 (80%) 24 g/5.4 g | 36% UC 36 g | 2% 2 g | 5% BISDMA 5 g | 27% DUDMA 27 g | .6 sweeter/ flavoring .6 g | Not paintable, no adherence |
| 12 | 25 (70%) 17.5/7 g | 24% UC 24 g | 3% 3 g | — | 49% DUDMA 49 g | .5% sweetener/ flavor .5 g | Very good paintability, good adherence, very good shine, very good smoothness. |
| 13 | 25 (80%) 20 g/4.5 g | 24% UC 24 g | 3% 3 g | — | 49% DUDMA 49 g | .5% sweetener/ flavor .5 g | Very good paintability, good adherence, very good shine, very good smoothness. |
| 14 | 25 (70%) 17.5/7 g | 24% UC 24 g | 3% 3 g | 10% BISDMA 10 g | 39% DUDMA 39 g | .5% sweetener/ flavor .5 g | Very good paintability, good adherence, good shine, very good smoothness. |

TABLE 1-continued

Exemplary Compositions

| # | Rosin (note 0) | Whitener | Initiator (note 1) | Crosslinker | Resin | Other | Comments |
|---|---|---|---|---|---|---|---|
| 15 | 25 (80%) 20 g/4.5 g | 24% UC 24 g | 3% 3 g | 10% BISDMA 10 g | 39% DUDMA 39 g | .5% sweetener/ flavor .5 g | Paintable, good adherance, good shine, very good smoothness |
| 16 | 25 (60%) 17 g/7 g | 24% UC 24 g | 3% 3 g | 20% BISDMA 20 g | 29% DUDMA 29 g | .5% sweetener/ flavor .5 g | Paintable, poor adhesion, no shine, very good smoothness |
| 17 | 25 (80%) 20 g/4.5 g | 24% UC 24 g | 3% 3 g | 20% BISDMA 20 g | 29% DUDMA 29 g | .5% sweetener/ flavor .5 g | Paintable, poor adhesion, no shine, very good smoothness |
| 18 | 25% (70%) 17.5/7.5 g | 27% 27 g | UC 3 g | 8% BISDMA 8 g | 32% DUDMA 32 g | 5% NaF 5 g | paintable, smooth, poor adhesion |

Note 0: Rosin mixture is recorded as % rosin/solvent mixture. 25 (70%) is 25% of 70% rosin/ethanol mixture, or 17.5 g rosin and 7.5 g solvent. The solvent is ethanol unless otherwise specified. Where sweetener/flavoring is used, this % is considered part of the gross solvent amounts (the sweetener/flavoring is mostly solvent by weight).
Note 1: Unless otherwise noted, the initiator is diphenyl(2,4,6-trimethylbenzoyl) phosphine oxide.
Note 2: Weights are in grams, in 100 g of compound.

Table 2 demonstrates experiments to determine the attributes of compounds that have fluoridation, alternative (to UC) whitening compounds, and other colorant compounds added to the formulation.

| # | Rosin (note 0) | Whitener | Initiator (note 1) | Crosslinker | Resin | Other | Comments |
|---|---|---|---|---|---|---|---|
| A | 22% (70%) 15.4/6.6 g | 21% UC 21 g | 2% 2 g | 5% BISDMA 5 g | 45% DUDMA 45 g | 5% NaF | good workability, good adherence |
| B | 22% (70%) 15.4/6.6 g | 21% UC 21 g | 2% 2 g | 6% BISDMA 6 g | 40% DUDMA 45 g | 5% NaF 5 g 4% TiO2 4 g | Poor workability (thick) Poor set Looks good, thicker than optimal to apply, It removed stains, formed standard shell and left surface on part of tooth whiter which however is easily brushed off |
| C | 22% (70%) 15.4/6.6 g | 21% UC | 2% 2 g | 6% BISDMA 6 g | 40% DUDMA 40 g | 5% NaF 5 g 4% ACP 4 g | Great workability, sets well, not thick, bleached ok, no shine |
| E | 22% (70%) 15.4/6.6 g | 21% UC | 2% 2 g | 6% BISDMA 6 g | 40% DUDMA 40 g | 5% NaF 5 g 2% ACP 2 g 2% TiO2 2 g | Poor workability |

-continued

| # | Rosin (note 0) | Whitener | Initiator (note 1) | Crosslinker | Resin | Other | Comments |
|---|---|---|---|---|---|---|---|
| D | 23% (70%) 16.1/6.9 g | 24% UC | 2% 2 g | 6% BISDMA 6 g | 40% DUDMA 40 g | 5% NaF 5 g | Base, good workability, sets well, bleaches well. |
| F | 23% (70%) 16.1/6.9 g | 24% UC | 2% 2 g | 6% BISDMA 6 g | 40% DUDMA 40 g | 5% MPF 5 g | Very good workability and the tooth bleached nicely. Not FDA approved. |
| G | 23% (70%) 16.1/6.9 g | 24% Sodium Carbonate 24 g | 2% 2 g | 6% BISDMA 6 g | 40% DUDMA 40 g | 5% NaF 5 g | It was workable and did bleach the tooth. It was not great mixing with the rosin/ethanol |
| H | 23% (70%) 16.1/6.9 g | 24% Sodium Citrate 24 g | 2% 2 g | 6% BISDMA 6 g | 40% DUDMA 40 g | 5% NaF 5 g | This mixed better with rosin/ethanol mix. It was workable and did bleach tooth |
| I | 23% (70%) 16.1/6.9 g | 24% Potassium persulfate 24 g | 2% 2 g | 6% BISDMA 6 g | 40% DUDMA 40 g | 5% NaF 5% | It mixed well and was very good to work with. It also bleached the tooth effectively. |
| J | 23% (70%) 16.1/6.9 g | 24% Calcium Peroxide 24 g | 2% 2 g | 6% BISDMA 6 g | 40% DUDMA 40 g | 5% NaF 5% | Not paintable |

Note 0: Rosin mixture is recorded as % rosin/solvent mixture. 25 (70%) is 25g of 70% rosin/ethanol mixture, or 17.5 g rosin and 7.5 g solvent. The solvent is ethanol unless otherwise specified. Where sweetener/flavoring is used, this (%) is considered part of the gross solvent amounts (the sweetener/flavoring is mostly solvent by weight).
Note 1: Unless otherwise noted, the initiator is diphenyl(2,4,6- trimethylbenzoyl) phosphine oxide.
Note 2: Weights are in grams, in 100 g of compound.

The fluoridation compounds worked well as add-ins to the various compounds and do not appear to degrade the desired attributes of the in situ dental tray forming compound.

ACP as a remineralization compound mixed in, but did not create compound that was visually shiny.

The alternative solid whitening compounds replaced UC with varying degrees of success. Calcium peroxide produced an unpaintable compound.

Table 3 describes experiments with alternative initiator compounds and their effects on the in situ dental tray forming compound.

| # | Rosin (note 0) | Whitener | Initiator (note 1) | Crosslinker | Resin | Other | Comments |
|---|---|---|---|---|---|---|---|
| K | 22% (70%) 15.4/6.6 g | 33% UC 33 g | 3% 3 g | 6% BISDMA 6 g | 25% DUDMA 25 g 6% TEGDMA 6 g | 5% NaF 5 g | TEGDMA was added to try for a self-cure version. |
| L | 23% (70%) 16.1/6.9 g | 24% UC 24 g | 2% 2 g | 6% BISDMA 6 g | 40% DUDMA 40 g | 5% NaF 5 g | |

-continued

| # | Rosin (note 0) | Whitener | Initiator (note 1) | Crosslinker | Resin | Other | Comments |
|---|---|---|---|---|---|---|---|
| M | 30% (60%) 17.5/7.5 g | 30% UC 30 g | 2-3% 1 phenyl-1.2 propanedione 2-3 g | | 37-38% DUDMA 37-38 g | | The color of this product is like campheriquinone (yellow) but as it bleaches tooth it oxidizes and looks great. |
| | 30% (60%) 17.5/7.5 g | 30% UC 30 g | 2-3% Camp herquinone 2-3 g | | 37-38% DUDMA 37-38 g | | Yellow color, does not set evenly. |

Note 0: Rosin mixture is recorded as % rosin/solvent mixture. 25 (70%) is 25g of 70% rosin/ethanol mixture, or 17.5 g rosin and 7.5 g solvent. The solvent is ethanol unless otherwise specified. Where sweetener/flavoring is used, this % is considered part of the gross solvent amounts (the sweetener/flavoring is mostly solvent by weight).
Note 1: Unless otherwise noted, the initiator is diphenyl(2,4,6- trimethylbenzoyl) phosphine oxide.
Note 2: Weights are in grams, in 100 g of compound.

All of the alternative initiators listed provided acceptable attributes in the 2-3% range. Some of the compounds changed the color of the tray from clear/transparent to yellow.

Table 4 details formulations using aqueous 3% $H_2O_2$ as the whitener.

TABLE 4

Compounds Using Aqueous 3% $H_2O_2$ as Whitener

| # | Rosin (note 0) | Whitener | Initiator (note 1) | Resin | Comments |
|---|---|---|---|---|---|
| N | 30% (60%) 18/12 g | 18% $H_2O_2$ 4 g | 4% 4 g | 48% DUDMA 48 g | No set, no adherence |
| O | 30% (60%) 18/12 g | 27% $H_2O_2$ 4 g | 4% 4 g | 39% DUDMA 39 g | No set, no adherence, not smooth |
| P | 30% (60%) 18/12 g | 36% $H_2O_2$ 4 g | 4% 4 g | 30% DUDMA 30 g | No set, unpaintable, no adherence, not smooth on tooth. |
| Q | 30% (80%) 24/6 g | 18% $H_2O_2$ 4 g | 4% 4 g | 48% DUDMA 48 g | No set |
| R | 30% (80%) 24/6 g | 27% $H_2O_2$ 4 g | 4% 4 g | 39% DUMA 39 g | No set, no adherence, no shine, not smooth on tooth |
| S | 30% (80%) 24/6 | 36% $H_2O_2$ 4 g | 4% 4 g | 30% DUDMA 30 g | No set, not paintable, no adherence, no shine, not smooth on tooth |

Note 0:
Rosin mixture is recorded as % rosin/solvent mixture. 25 (70%) is 25g of 70% rosin/ethanol mixture, or 17.5 g rosin and 7.5 g solvent. The solvent is ethanol unless otherwise specified. Where sweetener/flavoring is used, this % is considered part of the gross solvent amounts (the sweetener/flavoring is mostly solvent by weight).
Note 1:
Unless otherwise noted, the initiator is diphenyl(2,4,6-trimethylbenzoyl) phosphine oxide.
Note 2:
Weights are in grams, in 100 g of compound.

Aqueous $H_2O_2$ prevents setting in all formulations. Aqueous $H_2O_2$ can not be used in an in situ dental tray forming compound.

Tables 5 and 6 details compound formulations using alternative resins and resin combinations.

TABLE 5

Compositions Using Alternative Resins and Resin Combinations

| # | Rosin | Whitener | Initiator (note 1) | Resin | Comments |
|---|---|---|---|---|---|
| T | 40% (80%) 32/8 g | 25% UC 25 g | 10% 10 g | 25% TEGDMA 25 g | This is a good product (all attributes good or better). Easy to mix and shake. |
| U | 40% (80%) 32/8 g | 20% UC 20 g | 10% 10 g | 30% TEGDMA 30 g | This is good product too. |
| V | 30% (80%) 24/6 g | 20% UC 20 g | 5% 5 g | 30% DUDMA 30 g 15% TEGDMA 15 g | Thin mix, clumpy |
| W | 50% (80%) 40/10 g | 25% UC 25 g | 5% 5 g | 20% TEGDMA 20 g | Very workable, thin mix. clumpy. |

TABLE 5-continued

Compositions Using Alternative Resins and Resin Combinations

| # | Rosin | Whitener | Initiator (note 1) | Resin | Comments |
|---|---|---|---|---|---|
| X | 50% (80%) 40/10 g | 25% UC 25 g | 5% 5 g | 10% DUMA 20 g 10% TEGDMA 10 g | This painted on better, more control, still a little clumpy. The addition of the resin made a more controllable mix but will be thicker. |
| Y | 45% (80%) 36/9 g | 30% UC 30 g | 5% 5 g | 10% DUDMA 10 g 10% TEGDMA 10 g | Ground UC, clumper than T. UC reclumped after mixing. |

Note 0:
Rosin mixture is recorded as % rosin/solvent mixture. 25 (70%) is 255 of 70% rosin/ethanol mixture, or 17.5 g rosin and 7.5 g solvent. The solvent is ethanol unless otherwise specified. Where sweetener/flavoring is used, this % is considered part of the gross solvent amounts (the sweetener/flavoring is mostly solvent by weight).
Note 1:
Unless otherwise noted, the initiator is diphenyl(2,4,6-trimethylbenzoyl) phosphine oxide.
Note 2:
Weights are in grams, in 100 g of compound.

The experiments demonstrated using alternative compounds and resin/rosin combinations. The resulting combinations were still clumpy until we added mineral oil to the formulations. The learning is the resin/rosin combinations require specific ratios of resin/rosin and if using a solid whitening compound, the resulting formulation must have a mechanism to address the clumping of the solids in the mixture.

TABLE 6

Alternative formulations

| # | Rosin (note 0) | Whitener | Initiator (note 1) | Resin | Other | Comments |
|---|---|---|---|---|---|---|
| AA | 55% (80%) 44/11 g | 20% UC 20 g | 5% 5 g | 10% DUDMA 10 g 10% TEGDMA 10 g | — | (Clumpy) |
| DD | 25% (80%) 20/5 g | 25% UC 25 g | 5% 5 g | 15% DUDMA 15 g 30% TEGDMA 30 g | — | Good workability |
| EE | 20% (80%) 16/4 g | 40% UC 40 g | 4% 4 g | 36% TEGDMA 36 g | — | (Too clumpy) |
| FF | 25% (80%) 20/5 g | 35% UC 35 g | 4% 4 g | 36% TEGDMA 36 g | — | Good product |
| GG | 25% (80%) 20/5 g | 25% UC 25 g | 5% 5 g | 15% DUDMA 15 g 30% TEGDMA. 30 g | — | Good product |
| HH | 25% (80%) 20/5 g | 35% UC 35 g | 3% 3 g | 25% DUDMA 25 g | 12% MOIL 12 g | Active, smooth, and worked quickly |
| II | 40% (80%) 32/8 g | 30% UC 30 g | 3% 3 g | 20% DUDMA 20 g | 7% MOIL 7 g | Loosens quickly (low adhesion) |
| JJ-1 | 20% (80%) 16/4 g | 30% UC 30 g | 3% 3 g | 40% DUDMA 40 g | 7% MOIL 7 g | Good product |
| JJ-2 | 20% (80%) 16/4 g | 30% UC 30 g | 7% 2 g | 40% DUDMA 40 g | 8% MOIL 8 g | Good product |
| KK | — | 30% UC 30 g | 3% 3 g | 60% DUDMA 60 g | 7% MOIL 7 g | Very poor adherence (flakes off) |
| LL | 19% (80%,) 15.2/3.8 g | 27% UC 27 g | 1.5% 1.5 g | 39% DUDMA 39 g | 13.5% MOIL 13.5 g | Really smooth and much easier to apply. Nothing settled, |

TABLE 6-continued

Alternative formulations

| # | Rosin (note 0) | Whitener | Initiator (note 1) | Resin | Other | Comments |
|---|---|---|---|---|---|---|
| MM | 12.5% (80%) 10/2.5 g | 40% UC 40 g | 1.5% 1.5 g | 26% DUDMA 26 g | 20% MOIL 20 g | Like LL, rougher to touch than LL, but still good. |

Note 0: Rosin mixture is recorded as % rosin/solvent mixture. 25 (70%) is 255 of 70% rosin/ethanol mixture, or 17.5 g rosin and 7.5 g solvent. The solvent is ethanol unless otherwise specified. Where sweetener/flavoring is used, this % is considered part of the gross solvent amounts (the sweetener/flavoring is mostly solvent by weight).
Note 1: Unless otherwise noted, the initiator is diphenyl(2,4,6- trimethylbenzoyl) phosphine oxide.
Note 2: Weights are in grams, in 100 g of compound.

The alternative formulation experiments demonstrated that compounds with less than 20% rosin and 25-40% UC mixed with mineral oil in a 2:1 ratio provided optimal tray-forming attributes.

Table 7 shows the effects of using alternative oils (to mineral oil) in the compound. The rosin/resin/oil ratios control setting, as does the type of oil. Mineral oil and sunflower oil are preferred oils, although all oils appear to work in the compound.

TABLE 7

Alternative Oils in Compounds

| # | Rosin (note 0) | Resin | Other | Comments |
|---|---|---|---|---|
| O1 | 33 (80%) 26.4/3.6 g | 33% DUDMA 33 g | 33% MOIL 33 g | No set |
| O2 | 39.6 (80%) 31.68/7.92 g | 26.4% DUDMA 26.4 g | 33% MOIL 33 g | Good set |
| O3 | 39.6 (80%) 31.68/7.92 g | 33% DUDMA 33 g | 33% sunflower oil | Good set |
| O4 | 39.6 (80%) 31.68/7.92 g | 33% DUDMA 33 g | 33% vitamin E oil | Sets fairly |
| O5 | 39.6 (80%) 31.68/7.92 g | 33% DUDMA 33 g | 33% olive oil (cold pressed, extra virgin) | Sets fairly |

Note 0:
Rosin mixture is recorded as % rosin/solvent mixture. 25 (70%) is 255 of 70% rosin/ethanol mixture, or 17.5 g rosin and 7.5 g solvent. The solvent is ethanol unless otherwise specified. Where sweetener/flavoring is used, this % is considered part of the gross solvent amounts (the sweetener/flavoring is mostly solvent by weight).
Note 2:
Weights are in grams, in 100 g of compound.

Table 8 illustrates the use of other therapeutic compounds added into the in situ dental tray forming compound. Both compounds tests were analgesics.

TABLE 8

Therapeutic Compounds

| # | Rosin (note 0) | Whitener | Initiator (note 1) | Resin | Other | Comments |
|---|---|---|---|---|---|---|
| D0 | 15% (80%) 12 g/3 g | 40% UC 50 g | 2% 2 g | 23% DUDMA 23 g | 20% sunflower oil (1/2 of UC) 20 g | |
| D1 | 30% (80%) 24 g/6 g | — | 2% 2 g | 28% DUDMA 28 g | 40% benzocaine (alcohol soluble) 40 g | |
| D2 | 30% (80%) 24 g/6 g | 13.5% UC 13.5 g | 2% 2 g | 28% DUDMA 28 g | Mineral oil, 6.5g (5.4%) 40% benzocaine - 40g (33.3%) | (in 120 g of compound) |
| D3 | 16% (80%) 12.8/ 3.2 g | — | 2% 2 g | 22% DUDMA 22 g | 40% ibuprofen in 20% sunflower oil 40g ibuprofen 20g sunflower oil | |

Note 0: Rosin mixture is recorded as % rosin/solvent mixture. 25 (70%) is 255 of 70% rosin/ethanol mixture, or 17.5 g rosin and 7.5 g solvent. The solvent is ethanol unless otherwise specified. Where sweetener/flavoring is used, this % is considered part of the gross solvent amounts (the sweetener/flavoring is mostly solvent by weight).
Note 1: Unless otherwise noted, the initiator is diphenyl(2,4,6-trimethylbenzoyl) phosphine oxide.
Note 2: Weights are in grams, in 100 g of compound unless otherwise noted.

Two preferred compound formulations were identified from the experiments. These compound formulations appear to function well over well defined ranges and support the add-in of cosmetic and therapeutic compounds without substantial changes in formulation. These compounds can be generalized as:

Compound NN 10-40% UC, ½ UC in oil, rosin/resin in 1:2 (80% resin) mix, 1.5% initiator, 0.5% mint.

Compound PP 10-40% UC, ½ UC in oil, rosin/resin in 2:3 (80% resin) mix, 1.5% initiator, 0.5% mint.

Variations of operable formulations for each of the compounds are detailed in Table 9 and 10.

TABLE 9

Production Compounds in 1:2 Rosin/Resin (80% Resin) Mixture, Various UC Concentrations in the range of 10-40%..

| ID | UC (% and g) | Oil (% and g) | Initiator (% and g) (note 1) | Flavoring (% and g) | Resin (g) (note 3) | Rosin (80% mix) (resin/eth) g) |
|---|---|---|---|---|---|---|
| NN-1 | 10 | 5 | 1.5 | .5 | 55.3 | 27.7 (22.2/5.5) |
| NN-2 | 15 | 7.5 | 1.5 | .5 | 50.3 | 25.2 (20.2/5) |
| NN-3 | 20 | 10 | 1.5 | .5 | 45.7 | 22.3 (17.8/4.5) |
| NN-4/ LL | 25 | 12.5 | 1.5 | .5 | 40.3 | 20.2 (16.2/4) |
| NN-5 | 30 | 15 | 1.5 | .5 | 35.3 | 17.7 (14.2/3.5) |
| NN-6 | 35 | 17.5 | 1.5 | .5 | 31 | 15.5 (12.4/3.1) |
| NN-7/ MM | 40 | 20 | 1.5 | .5 | 25.3 | 12.7 (10.1/2.6) |

Note 0: Rosin mixture is recorded as % rosin/solvent mixture. 25 (70%) is 255 of 70% rosin/ethanol mixture, or 17.5 g rosin and 7.5 g solvent. The solvent is ethanol unless otherwise specified. Where sweetener/flavoring is used, this % is considered part of the gross solvent amounts (the sweetener/flavoring is mostly solvent by weight).
Note 1: Unless otherwise noted, the initiator is diphenyl(2,4,6- trimethylbenzoyl) phosphine oxide.
Note 2: Weights are in grams, in 100 g of compound
Note 3: Resin used is DUDMA.

TABLE 10

Production Compounds in 3:2 Rosin/Resin (80% Resin) Mixture, Various UC Concentrations in the range of 10-40%,

| ID | UC (% and g) | Oil (% and g) | Initiator (% and g) (note 1) | Flavoring (% and g) | Resin (g) (note 3) | Rosin (80% mix) (resin/eth) (g) |
|---|---|---|---|---|---|---|
| PP-1 | 10 | 5 | 1.5 | .5 | 49.8 | 33.2 (26.6/6.6) |
| PP-2 | 15 | 7.5 | 1.5 | .5 | 45.3 | 30.2 (24.2/6) |
| PP-3 | 20 | 10 | 1.5 | .5 | 40.8 | 27.2 (21.8/5.4) |
| PP-4 | 25 | 12.5 | 1.5 | .5 | 36.3 | 24.2 (19.4/4.8) |
| PP-5 | 30 | 15 | 1.5 | .5 | 31.8 | 21.2 (17/4.2) |
| PP-6 | 35 | 17.5 | 1.5 | .5 | 27.9 | 18.6 (14.9/3.7) |
| PP-7 | 40 | 20 | 1.5 | .5 | 77.8 | 15.2 (12.2/3) |

Note 0: Rosin mixture is recorded as % rosin/solvent mixture. 25 (70%) is 255 of 70% rosin/ethanol mixture, or 17.5 g rosin and 7.5 g solvent. The solvent is ethanol unless otherwise specified. Where sweetener/flavoring is used, this % is considered part of the gross solvent amounts (the sweetener/flavoring is mostly solvent by weight).
Note 1: Unless otherwise noted, the initiator is diphenyl(2,4,6-trimethylbenzoyl) phosphine oxide.
Note 2: Weights are in grams, in 100 g of compound.
Note 3: Resin used is DUDMA.

5.9 Experiments

In situ tray forming compounds were tested for elution of add-in compounds (whitening and therapeutic) in order to determine if the in situ tray structures were able to functionally release these compounds, and to determine their effectiveness relative to other commercially available products. All experiments showed that the compounds tested eluted the active compounds at rates that made them at least as effective as other commercial options, and that the in situ formed tray released after the elution was completed.

The rate of release of in situ formed trays is dependent upon the specific formulation and the amount of water or ethanol available to facilitate the release. In an experiment, compounds NN-1, NN-3, NN-5, NN-7, and PP-4 were tested side by side on a moistened porous tile substrate. The set compounds started to lose structural integrity at 15 minutes (solely from the water in the tile and from water generated by the UC activation), and released completely within 80 minutes.

Subsequent in-vivo testing indicates the breakdown and release times to be about 15 minutes in an oral cavity, and much shorter if the compounds are actively rinsed with water or Listerine. Rinsing with water or Listerine accelerates the release and activation of the active compounds and dilutes the rosin embedded within the in situ tray's polymer matrix. The release and activation of the compounds and removal of the rosin weakens the polymer matrix, resulting in the set tray losing structural integrity and causing its release from the underlying surface (and breaking up).

5.10 Packaging

The in situ dental tray forming compound may be packed in a 3 g or 4 g one or two barrel syringe (depending upon the active ingredients and their interactions), or in blister packs of the same approximate weight.

5.11 Use

The hardened (set) form of the in situ dental tray (unlike dental varnishes described above) is a hard, smooth, transparent shell that covers the oral surface, typically the teeth, but may include cold sores, denture sores and irritation, herpes lesions, burns and apthous ulcers. The add-ins (e.g., bleaching agent) are retained intimately close to the oral surface, which prevents the add-in compounds from leaching into the patients mouth and irritating the mouth or gums. The following describes example use of the tray forming compound to form a tray and apply a whitening treatment to a patients teeth.

The in situ dental forming tray compound, such as the compound shown as compound 1 above, is utilized by an oral care practitioner (e.g., dentist, hygienist) by first drying the teeth using compressed air as known by these practitioners. The in situ dental tray forming compound is applied to individual or sets of teeth (or other oral surfaces) using a suitable applicator (such as a brush), and the applied in situ dental tray forming compound and teeth are then exposed to UV light using a standard dental UV curing light.

Without being bound to any particular theory of action, the light exposure causes the in situ dental tray forming compound to harden (set) into a transparent dental tray affixed to the teeth (or other oral surface). Setting occurs when the compound polymerizes under the effects of the dental UV curing light. Once set, the dental tray begins to elute the active compounds. As the dry teeth still contain some moisture, the retained moisture reacts with the bleaching agent in the in situ formed dental tray to decompose the bleaching agent (carbamide peroxide) into urea and hydrogen peroxide. The hydrogen peroxide subsequently decomposes into water and an oxygen radical. The oxygen radical bleaches staining on the teeth, the water serves as a continuing solvent to further dissolve and decompose the bleaching agent contained within the in situ formed dental tray. The desolution-decomposition of the carbamide peroxide into an oxygen radical is the activation of the carbamide peroxide in the compound. To accelerate the process, the dental professional may wet the teeth prior to application of the in situ dental tray forming compound to the teeth instead of drying them. The water also serves to weaken the structure of the in situ formed dental tray by diluting the resin. This results in the release and activation of additional bleaching agents and further weakens the bond between the formed tray and the teeth to which it is applied. The compound is formulated to complete effective bleaching about the time that bond between the in situ formed tray and the teeth releases, causing the in situ formed tray to detach from the teeth. Depending upon the thickness of the tray, the tray may optionally disintegrate into small pieces. The amount of time that the in situ formed dental tray remains attached to the teeth may be further controlled by subsequent rinsing with water, ethanol, or an ethanolic mouthwash (e.g. Listerine). In this way, a complete bleaching treatment may be provided in a little as 10 minutes (from application to breakdown of the tray), and the dental practitioner may repeat the above process to perform additional treatments during the same office visit. The table below includes in situ formed dental tray using the PP-4 compound from time of setting until it releases used various oral conditions.

| Condition | Release Time |
|---|---|
| Basic tray w/ dried teeth | 30 minutes |
| Basic tray w/ moistened teeth | 20 minutes |
| Basic tray w/ rinsing with water (every 5 minutes) | 20 minutes |
| Basic tray w/ rinsing with water (every 2 minutes) | 12.5 minutes |
| Basic tray w/ rinsing with Listerine (every 5 minutes) | 20 minutes |

| Condition | Release Time |
| --- | --- |
| Basic tray w/ rinsing with Listerine (every 2 minutes) | 12.5 minutes |
| Basic tray w/ rinsing with water for 30 seconds at 1 minute intervals | 5-7 minutes (depending upon thickness of tray) |
| Basic tray w/ continuous rinsing with water | 90 seconds |

As is evident from the above table, the in situ formed dental tray can be applied and self-removed at differing time intervals based upon the specific compound formulation selected and the application method.

A significant advantage to the in situ dental tray process described above is that it does not cause oral pain from the use of oxidizing chemicals on sensitive tissues, nor does it cause tooth pain as commonly reported with other dental tooth whitening products. The in situ dental tray setting process creates a hard structures that limits the spread of the oxidizing chemicals in the oral cavity by encapsulating them. The compound is designed to break down as it is exposed to moisture, providing a selectable rate of time release of the active compound(s) into the oral cavity.

In addition to being colorless, the dental tray compounds disclosed herein are also transparent.

Example 1—Patient, 3 Cycles in One Hour (20 Minutes Per Tray)

A patient was treated with compound PP-4, following the application instructions above. No rinsing was performed. The in situ formed dental tray decomposed and released in approximately 20 minutes. The process was repeated 2 more times, resulting in 3 treatments using the compound over course of an hour. No oral or dental pain was reported and visible whitening of the treated teeth was observed.

The patient returned in one week and was treated again using compound PP-4. The patient rinsed every 2-3 minutes with water. This shortened the decomposition and release time to approximately 7 minutes. The treatment process was repeated 2 more times, resulting in 3 treatments using the compound over the course of 30 minutes. No oral or dental pain was reported and visible whitening of the treated teeth was observed.

Example 2—Patient, 3 Cycles in 30 Minutes

A patient was treated with compound PP-4, following the application instructions above. The patient rinsed with water every 1-2 minutes, and ethanol was painted on the tray after rinsing. The in situ formed dental tray decomposed and released in approximately 7 minutes. The process was repeated 2 more times, resulting in 3 treatments using the compound over course of 30 minutes. No oral or dental pain was reported and visible whitening of the treated teeth was observed.

Example 3—Patient, 3 Cycles in 30 Minutes

A patient was treated with compound PP-4, following the application instructions above. The patient rinsed with water every 90 seconds with a 50/50 water/Listerine mixture. The in situ formed dental tray decomposed and released in approximately 7 minutes. The process was repeated 2 more times, resulting in 3 treatments using the compound over course of 30 minutes. No oral or dental pain was reported and visible whitening of the treated teeth was observed.

Example 4—Patent, 4 Cycles Over 45 Minutes

A patient was treated with compound PP-4, following the application instructions above. The patient rinsed with water every 90 seconds with water. The in situ formed dental tray decomposed and released in approximately 7 minutes. The process was repeated 3 more times, resulting in 4 treatments using the compound over course of 45 minutes. No oral or dental pain was reported and visible whitening of the treated teeth was observed.

Example 5—Patient 5, Therapeutic Release

A patient was treated with compound D1 by applying the compound to an oral surface in accordance with instructions. Within 3 minutes, the benzocaine in the compound had numbed the oral surface.

CONCLUSION

The above description of the embodiments, alternative embodiments, and specific examples, are given by way of illustration and should not be viewed as limiting. Further, many changes and modifications within the scope of the present embodiments may be made without departing from the spirit thereof, and the present invention includes such changes and modifications.

What is claimed:

1. A dental tray composition for treating the teeth of a patient with a surface dental treatment, comprising:
   at least one rosin, said at least one rosin being at least partially hydrogenated;
   at least one acrylic type resin;
   a solvent; and
   at least one of a whitening agent or a fluoridating agent;
   said at least one rosin and said at least one acrylic type resin being combined in a ratio effective to enable said dental tray composition to polymerize and form in situ a substantially hardened shell on the surfaces of said teeth of said patient, and substantially release said substantially hardened shell from the surfaces of said teeth upon the substantial completion of the elution of said at least one whitening agent or said fluoridating agent from said dental tray composition.

2. The dental tray composition of claim 1, wherein activation of said dental tray composition is effective to initiate said elution, and said elution weakens said dental tray composition to enable said release upon said substantial completion of said elution.

3. The dental tray composition of claim 1, further comprising a cross-linker.

4. The dental tray composition of claim 1, further comprising a re-mineralizing agent.

5. The dental tray composition of claim 1, further comprising a flavor additive.

6. The dental tray composition of claim 1, further comprising a sweetener.

7. The dental tray composition of claim 1, further comprising an anti-cavity agent.

8. The dental tray composition of claim 7, wherein said anti-cavity agent is a silver-based agent.

9. The dental tray composition of claim 1, wherein said rosin is at least partially hydrogenated.

10. The dental tray composition of claim 9, wherein said rosin is fully hydrogenated.

11. The dental tray composition of claim 10, wherein said rosin has an acid number (AN) of 165.

12. The dental tray composition of claim 1, wherein said at least one acrylic type resin is selected from the group consisting of: 2-Hydroxyethyl methacrylate (HEMA), 2-(Dimethylamino) ethyl methacrylate, Isobornyl methacrylate, Methyl methacrylate, 3-(Trimethoxysilyl) propyl methacrylate, (Trimethylsilyl) methacrylate, 3-(Tris (trimethylsiloxy) silyl) propylmethacrylate, 2-(Trimethylsilyloxy) ethyl methacrylate, diurethane dimethacrylate (DUDMA), triethylene glycol dimethacrylate (TEGDMA), bisphenol A glycerolate dimethacrylate (BISDMA), Ethylene glycol dimethacrylate (EGDM), Biphenyl dimethacrylate (BPDM), 1,6-Hexanediol dimethacrylate (HDMA), Tetraethylene glycol dimethacrylate, Bisphenol A glycerolate dimethacrylate, 9 Bisphenol A glycerolate diacrylate, Glycerol 1, 3-dimethacrylate (CDMA), 9 Polyethylene glycol diacrylates, Dipentaerythritol penta-hexa-acrylate, Ethoxylated bisphenol methacrylate (EBPADMA), Bisphenol A ethoxylate diacrylate, and Trimethylolpropane trimethacrylate (TMPTMA).

13. The dental tray composition of claim 1, wherein said acrylic type resin comprises a mixture of an acrylic type resin and bisphenol A.

14. The dental tray composition of claim 12, wherein said acrylic type resin further comprises an initiator.

15. The dental tray composition of claim 14, wherein said initiator is diphenyl(2,4,6)trimethylbenzoyl phosphine oxide.

16. The dental tray composition of claim 15, wherein said acrylic type resin is diurethane dimetharylate.

17. The dental tray composition of claim 1, wherein said composition includes between about 10% and about 20% rosin, between about 22% and about 50% acrylic type resin, and between about 20% and about 40% whitening agent.

18. The dental tray composition of claim 17, further including between about 1.5% and about 10% of a cross-linker.

19. The dental tray composition of claim 18, wherein said composition includes between about 16% and about 18% rosin.

20. The dental tray composition of claim 19, wherein said composition includes between about 45% and about 50% acrylic type resin.

21. The dental tray composition of claim 20, wherein said composition includes about 5% cross-linker.

22. The dental tray composition of claim 21, wherein said composition includes about 24% whitening agent.

23. A method for treating or preventing dental caries and whitening teeth in a patient, comprising administering to said patient an effective amount of a dental tray composition of claim 1.

24. A dental tray composition for treating the teeth of a patient with a surface dental treatment, comprising:
   at least one rosin, said at least one rosin being at least partially hydrogenated;
   at least one acrylic type resin;
   an oil;
   a solvent; and
   a whitening agent; and
said at least one rosin and said at least one acrylic type resin being combined in a ratio effective to enable said dental tray composition to polymerize and form in situ a substantially hardened shell on the surfaces of said teeth of said patient, and substantially release said substantially hardened shell from the surfaces of said teeth upon the substantial completion of the elution of said at least one whitening agent or said fluoridating agent from said dental tray composition.

25. The dental tray composition of claim 24, wherein said resin:rosin ratio is between about 2:1 and about 3:2.

26. The dental tray composition of claim 25, wherein the ratio of said oil to said whitening agent is about 2:1 by weight.

27. The dental tray composition of claim 24, wherein said oil is less than 20% of the weight of said composition.

28. The dental tray composition of claim 27, wherein said whitening agent is urea-carbamide or carbamide peroxide.

29. The dental tray composition of claim 27, wherein said oil is about 5% by weight.

30. The dental tray composition of claim 29 that is described by formula NN-1 or formula PP-1.

\* \* \* \* \*